United States Patent [19]

Bertin et al.

[11] 4,301,366
[45] Nov. 17, 1981

[54] CHATTER DETECTION IN THICKNESS MEASURING GAUGES AND THE LIKE

[75] Inventors: Michale C. Bertin, Irvine, Calif.; Mark A. Carson, Stow, Ohio

[73] Assignee: Nucleonic Data Systems, Irvine, Calif.

[21] Appl. No.: 157,076

[22] Filed: Jun. 6, 1980

[51] Int. Cl.³ ............................................. G01N 23/00
[52] U.S. Cl. ..................................... 250/308; 250/359
[58] Field of Search .................... 250/308, 358 R, 359, 250/360

[56] References Cited

U.S. PATENT DOCUMENTS

| | | | |
|---|---|---|---|
| 3,257,559 | 6/1966 | McMullen | 250/308 |
| 3,479,511 | 11/1969 | Clerc | 250/308 |
| 3,766,386 | 10/1973 | Sivilotti et al. | 250/359 |
| 3,868,510 | 2/1975 | Murata et al. | 250/308 |
| 3,955,086 | 5/1976 | Tsujii et al. | 250/359 |

Primary Examiner—Alfred E. Smith
Assistant Examiner—Janice A. Howell

[57] ABSTRACT

Process and apparatus for measuring variations in a stream of material, such as thickness in a strip from a mill. A radiation source and detector are positioned at a gauging station. The stream of material moves past the station providing an electrical signal varying as a function of material at the station which signal includes a lower frequency component, a higher frequency cyclical component, and a higher frequency noise component. A circuit for providing a thickness output varying as a function of the lower frequency component of the signal, and a circuit providing an output indicating chatter varying as a function of the higher frequency cyclical component. Digital and analog versions are disclosed.

17 Claims, 5 Drawing Figures

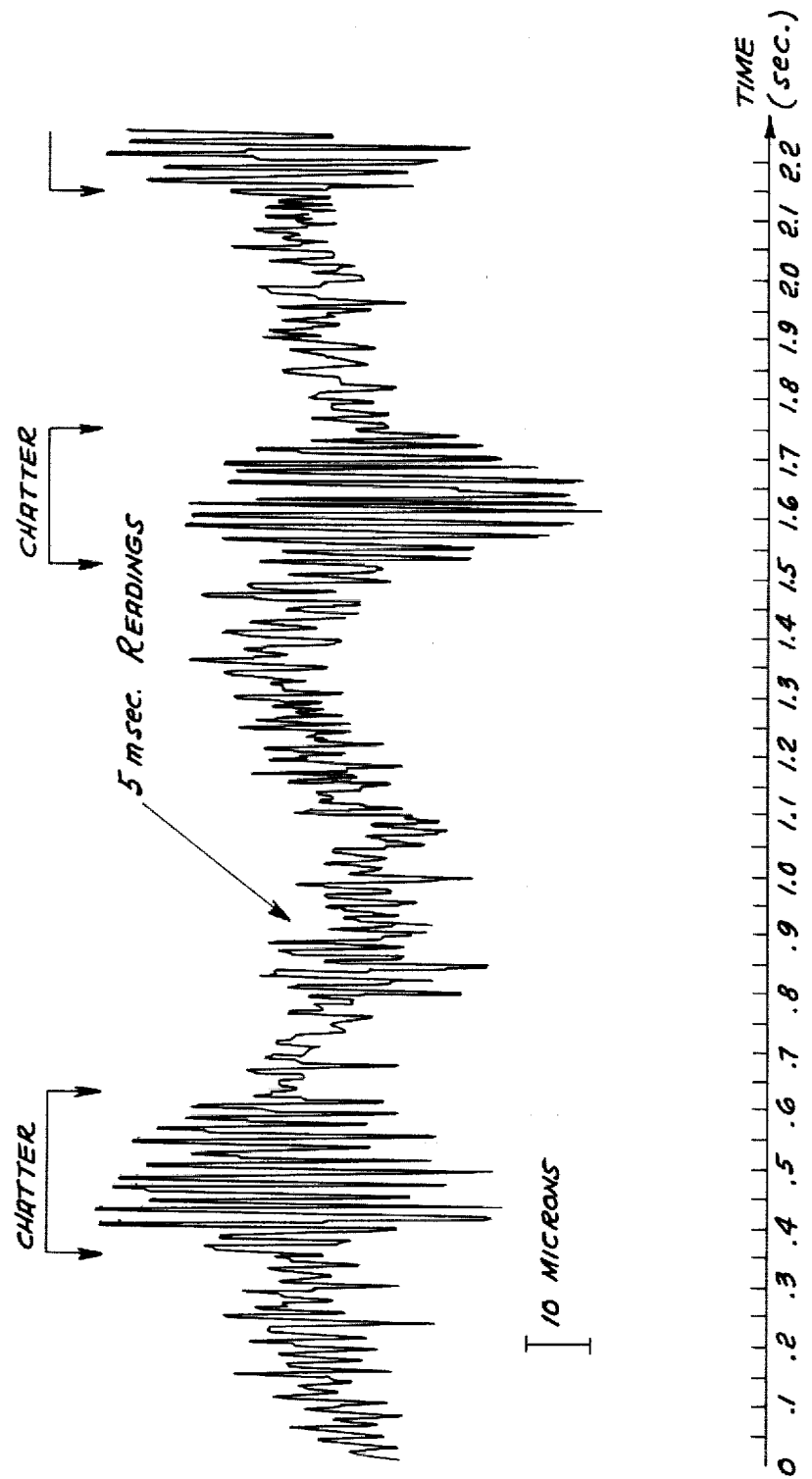

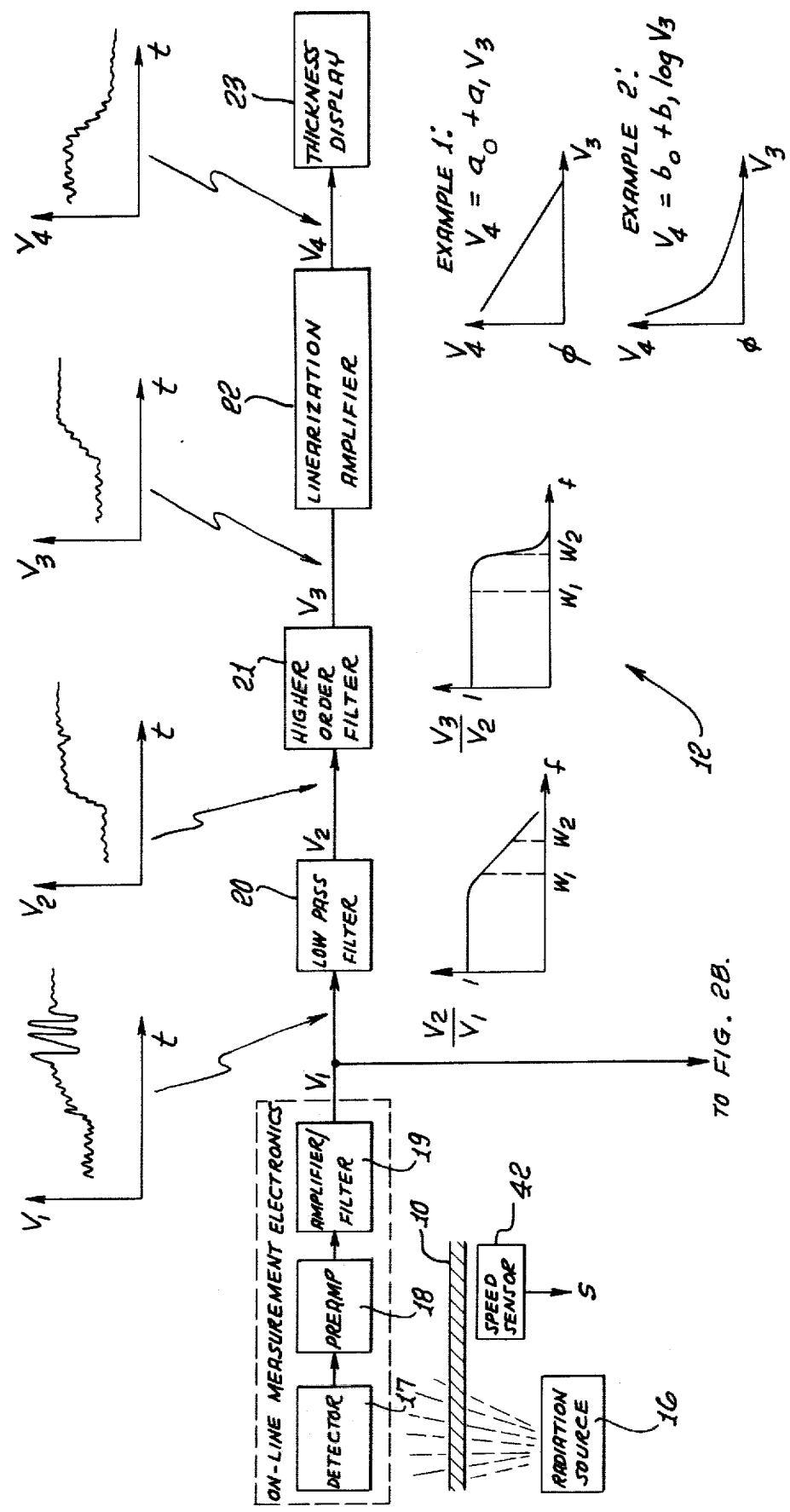

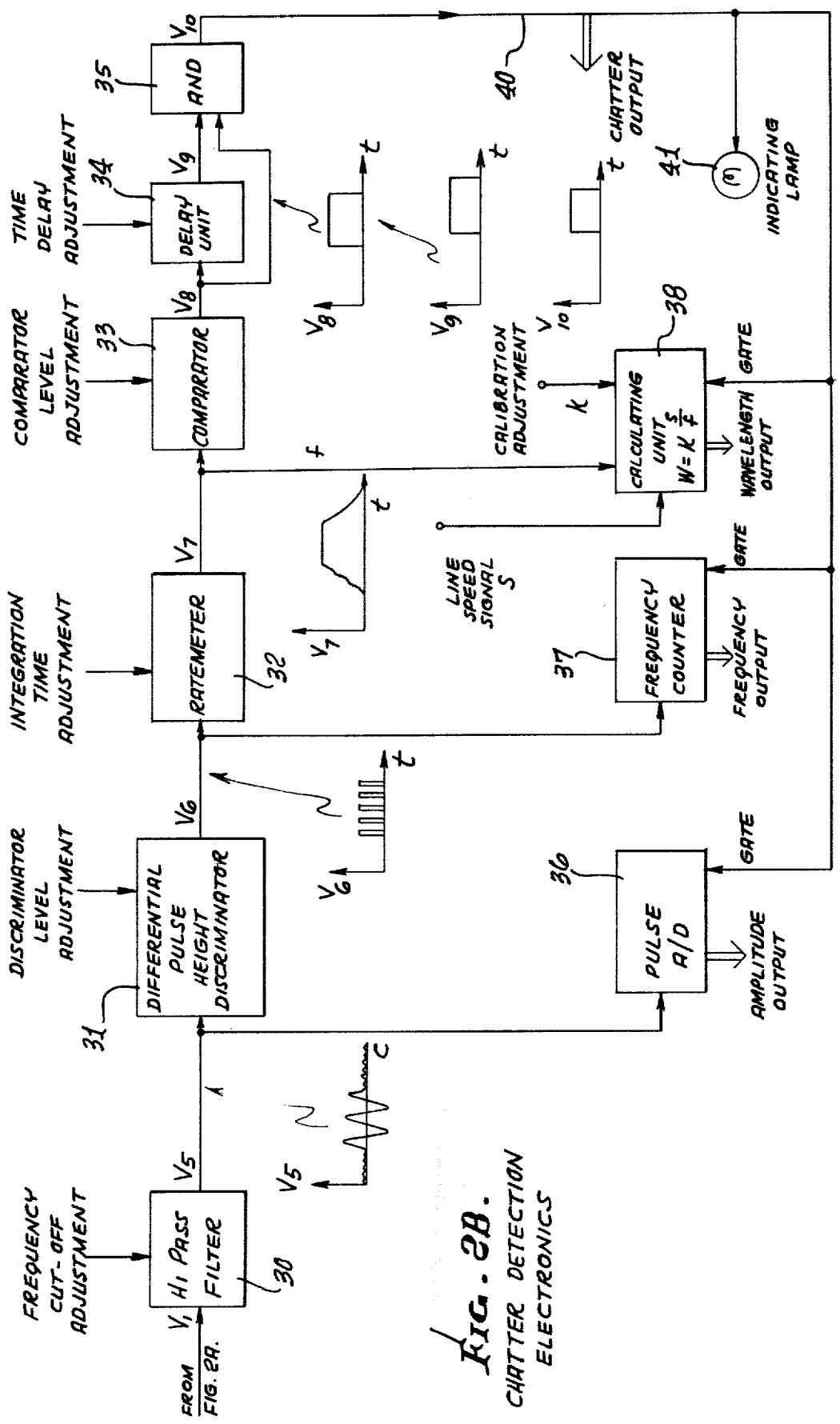

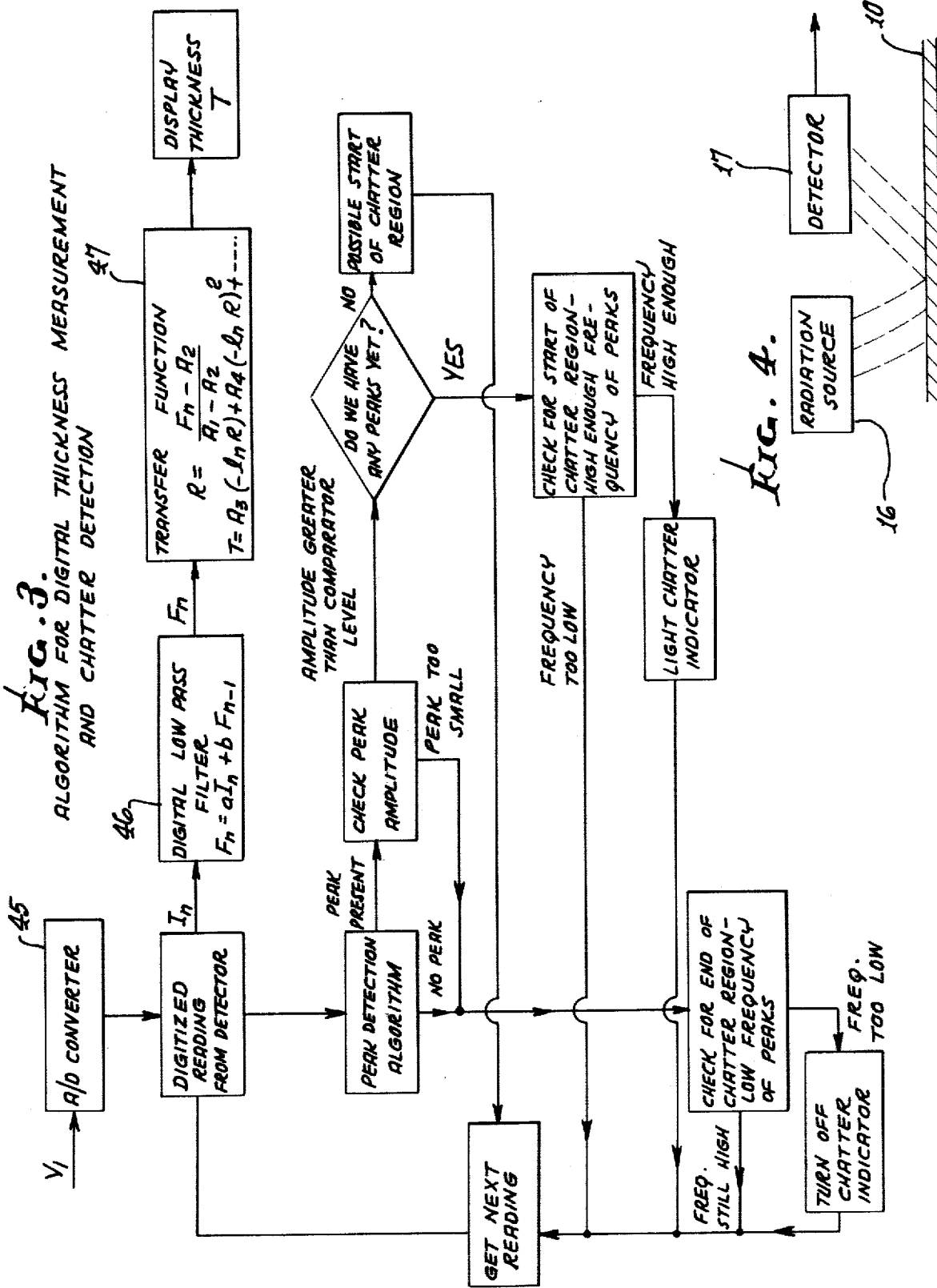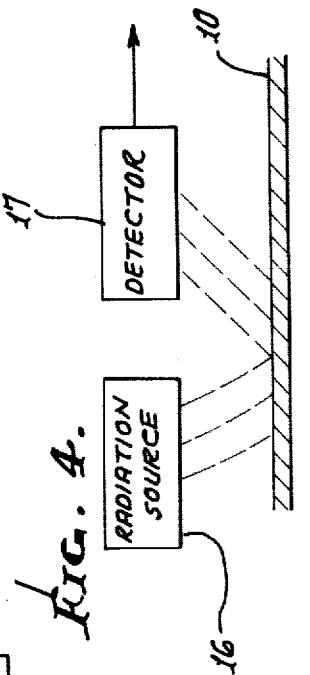

CHATTER DETECTION IN THICKNESS MEASURING GAUGES AND THE LIKE

BACKGROUND OF THE INVENTION

This invention relates to the detection of low frequency variations and high frequency cyclical variations in a signal, particularly those from on-line thickness measurement instruments.

Continuous processing of strip products such as steel, aluminum, rubber, paper, etc., has grown enormously over the past three decades. The quality of on-line instrumentation has improved correspondingly, and manufacturers are able to measure and control their processes within tighter and tighter tolerance bands. In many processes there are prolonged regions of high frequency variations in the product. An example is the thickness variation that occurs in the cold rolling of steel—in particular the phenomenon known as "chatter". A common cause of chatter is a mechanical resonance in the rolling mill which makes the rolls bounce. This gives rise to a thick (or thin) spot in the steel for each bounce. The thickness variations are a quality defect which may render the steel unsuitable for an end use such as can making.

Chatter may be characterized by the amplitude of the thickness variation and the spatial separation of the thick spots. For the roll bounce chatter described above, separations of 5-20 cm and amplitudes of 5-20 microns are found in 0.25 mm can stock. Such can stock is rolled at speeds from 600 to 2100 meters/minute, and finished on inspection, tinplating, and slitting lines at speeds from 300 to 600 meters/minute. The chatter shows up as high frequency variations in the range of 5 to 300 Hz. Regions of chatter may be as short as ten meters or as long as hundreds of meters. FIG. 1 shows an example of chatter, detected on a tinplating line with the strip of material moving at 500 meters/minute. The chatter is superposed on a much lower frequency variation in thickness, typically less than 2 Hertz.

Increasing concern on the part of the manufacturers has created the need to identify chatter on-line as part of the thickness measuring procedure. By identifying the chatter on a rolling mill it is possible to correct the cause of the chatter, and to identify the location of chatter within a coil of steel. On finishing lines the chatter can be cut out, or identified within the coil.

In conventional thickness gauges the thickness signals are integrated or filtered to improve the precision of the measurement. This smooths out the signal and destroys the chatter information. The present invention analyzes the signal prior to this integration and provides an output signal which identifies the presence of cyclical thickness variations such as chatter. The invention also provides means for identifying the amplitude and frequency of the chatter, and for calculating the spatial "wavelength" of the chatter. Such devices are not presently available, and the present invention represents a new type of instrumentation for on-line analysis of chatter.

While the example given above and the specific embodiments disclosed herein are for measurement of steel strip using a non-contacting nuclear thickness gauge, many other applications are possible using other non-contacting or contacting gauges, materials other than steel and properties other than thickness. The chatter detector is applicable to any continuous process in which there are high frequency signal variations. A very different example is measurement of optical density of liquids flowing through a pipeline.

SUMMARY OF THE INVENTION

In its broader concept, the invention provides apparatus and method for measuring variations in a stream of material moving relative to a gauging station. A sensor is positioned at the gauging station and produces an electrical signal varying as a function of material at the station with the signal including a lower frequency component, a higher frequency cyclical component, and a higher frequency noise component. The lower frequency component is utilized to provide a first output which typically is a measure of the long term changes in volume or thickness of the stream. The higher frequency cyclical component is used to provide a second output indicating presence of undesirable variations of a predetermined amplitude and frequency such as is produced by chatter in a rolling mill.

A more specific embodiment of the invention provides apparatus and method for measuring thickness variations in a strip of material moving relative to a gauging station. An electrical signal is produced by a sensor system such as a radioactive source and a radiation detector, with this signal having a lower frequency component, a higher frequency cyclical component, and a higher frequency noise component. In one branch, the higher frequency components are substantially removed and the lower frequency component is utilized to provide an output indicating the longer term variations in thickness of the product. In a second branch, the lower frequency component and the noise component are substantially removed and the higher frequency component is utilized to provide an output indicating chatter when the amplitude and frequency of this component exceed predetermined values.

In addition to indicating the presence of chatter, the magnitude of the chatter, the frequency of the chatter and the wavelength thereof may be determined and indicated. The system may be operated in the analog domain or in the digital domain as desired.

BRIEF DESCRIPTION OF THE DRAWINGS

FIG. 1 is a recording of the output obtained with a thickness gauge measuring a nominal 0.25 mm thick steel can stock moving at 500 meters per minute on a tin plating line;

FIGS. 2A and 2B is a block diagram illustrating a thickness and chatter measuring apparatus operating in analog style and incorporating the presently preferred embodiment of the invention;

FIG. 3 is an algorithm for a digital embodiment of the apparatus of FIGS. 2A and 2B; and FIG. 4 is a diagram similar to that of a portion of FIG. 2A illustrating a reflection type measuring system.

DESCRIPTION OF THE PREFERRED EMBODIMENTS

Referring to FIGS. 2A and 2B, a stream of material such as a strip of steel 10 is moved past a gauging station 11 which provides an output V1 having a lower frequency component, a higher frequency cyclical component, and a higher frequency noise component, as illustrated in FIG. 1. This output signal V1 is connected to thickness measuring electronics indicated generally at 12 and chatter detection electronics indicated generally at 13.

The gauging station may be a conventional on-line measurement unit such as a nuclear thickness gauge, a contacting thickness gauge, or any other type of instrumentation which produces the signal V1. The measuring instrument at the gauging station must have a response frequency which is greater than the frequency of the chatter to be detected. If a digital system is utilized to process the signals, the sampling rate must be high enough to prevent problems such as "aliasing".

In the preferred embodiment illustrated, a radioactive source 16 directs radiation through the strip 10 to a radiation detector 17. The output of the detector is connected to a preamplifier 18 which in turn is connected to an amplifier/filter 19 which provides the output V1. An alternative configuration utilizing reflection rather than transmission is illustrated in FIG. 4, with the radiation source 16 directed to the strip 10 and with the detector 17 measuring reflected radiation rather than transmitted radiation as in FIG. 2A.

The thickness measuring electronics 12, which may be conventional in nature, includes a lowpass filter 20, a higher order filter 21, a linerization amplifier 22, and a thickness display 23.

The lowpass filter 20 functions to remove high frequency components from the signal V1, producing the signal V2. The higher order filter 21 is preferred but not essential and is utilized to remove higher frequency noise such as microphonics, providing the output V3. The linerization amplifier is utilized to provide an output V4 which is directly proportional to thickness of the strip passing the gauging station. The linearization amplifier may take various forms, such as the linear amplifier shown in example 1 or the logarithmic amplifier shown in example 2. The signal V4 is then connected to the display unit 23 which may be a digital or analog meter or a printer or otherwise as desired, preferably providing a directly readable thickness indication.

The parameters w1 and w2 for the filters and a0, a1, b0 and b1 for the amplifier may vary depending upon the frequencies and amplitudes of the particular signals involved. The parameters may be set or may be made adjustable by means of potentiometers or switches.

The signal V4 is a direct indication of the longer term variation in thickness of the strip, corresponding to the lower frequency component of the signal V1. This is the component which is varying at about 1 Hertz in FIG. 1.

The preferred embodiment of the chatter detection electronics 13 illustrated in FIG. 2B includes a highpass filter 30, a differential pulse height discriminator 31, a rate meter 32, a comparator 33, a delay unit 34, and an AND gate 35. An analog to digital converter 36, a frequency counter 37, and a calculating unit 38 may also be included if desired. The inputs and outputs for the components 30-35 are indicated as V1 and V5-V10, with the waveforms for these various signals illustrated on the drawing. The components themselves may be conventional.

The highpass filter 30 removes the lower frequency component of the signal V1 including DC. The adjustable frequency cut-off input defines the passband of the filter.

The differential pulse height discriminator 31 performs amplitude selection on the pulses of signal V5. It generates an output V6 of uniform pulse height and width whenever the input signal V5 exceed a predetermined amplitude (the adjustable discriminator level), whether in the positive or negative directions. This level should be chosen to be just above the noise in signal V5. A level setting criterion may be set up in terms of how many times per second the noise will trigger this discriminator. Producing uniform pulses makes the subsequent chatter analysis independent of amplitude, and dependent only on the chatter frequency. Omitting this discriminator makes the chatter analysis dependent on the form of the chatter signal—its amplitude, frequency, and symmetry.

The ratemeter 32 produces an analog signal V7 whose amplitude is proportional to the chatter frequency, i.e., the pulse frequency of signal V6. To do this an integration time is chosen which is long compared with the expected period of the chatter. This integration time should be compatible with the cut-off frequency of the high pass filter 30.

The level of the comparator 33 is set to trigger an output at the desired frequency, i.e., when the amplitude of signal V7 exceeds a predetermined value. While a single comparator will suffice for most applications, two comparators may be used to produce an output only if the chatter is within a range of frequencies. This allows very high frequency chatter to be bypassed.

The delay unit 34 and AND gate 35 prevent indicating chatter output for very short regions of chatter. The size of the adjustable delay time establishes the minimum amount of chatter which will be indicated as chatter output at a given line speed. This delay suppresses a response to thickness transients, and insures that chatter is indicated only when there are repetitive signals of long enough duration. The delay may be made independent of line speed by setting the delay time inversely proportional to the line speed.

A typical figure for duration of a burst of chatter is in the range of 20 to 200 milliseconds. The corresponding delay provided by the delay unit 34 typically would be a few milliseconds. If the noise in the measuring system can be reduced, that is if the higher frequency noise component of the signal can be reduced, the delay time may also be reduced.

When there is coincidence in time of signals V8 and V9, as determined by the AND gate 35, signal V10 is produced on an output line 40, this signal being the one that indicates chatter as an output of the chatter detection electronics. The chatter output signal V10 may be used to actuate various types of indicators, such as an indicating lamp 41, and to initiate other operations, such as those carried out in units 36, 37 and 38.

The chatter output signal may be utilized to merely indicate that chatter is occurring. Alternatively, the chatter output signal may be coordinated with the strip of material to provide a record of where chatter occurs and/or to provide a marking on the strip indicating the zone in which chatter occurs. A principal source of chatter is bouncing of rolls in the rolling stand. This is in contrast to thickness variations measured by the thickness measuring electronics 12, which thickness variations usually occur due to eccentricity of a roll or to variations in setting of a roll. The thickness signal V4 may be utilized solely for display and informational purposes or may be used to provide automatic control of roll stand settings.

Chatter amplitude information may be obtained by using the pulse A/D convertor 36 with the output V5 of the highpass filter 30 as the input. The operation may be limited to those times when chatter is present by using the chatter output signal V10 on line 40 as a gating signal.

Chatter frequency information may be obtained by counting the output V6 of the pulse height discriminator 31 in the counter 37. This frequency counter may be gated with the chatter output signal 40 to insure a display only when chatter is present.

The wavelength, or spatial separation of the chatter thick spots may be obtained in calculating unit 38 whose inputs are the signal f (V7), proportional to the frequency of the chatter, and a signal s from a speed sensor 42 (FIG. 2A), proportional to the speed of the strip 10 relative to the gauging station 11. The wavelength, w, may be calculated using the relationship $w = k \cdot s/f$, where k is a calibration constant.

Various types of output signals may be used for the chatter, chatter amplitude, chatter frequency and chatter wavelength outputs. These include signals which may be analog or digital in form, and which may be displayed in meters or presented as voltage or current signals.

In the preferred embodiment, two comparator levels are used for the differential pulse height discriminator 31, with one set at a positive value and the other at a negative value. Then an output pulse for signal V6 is provided for both positive going and negative going variations in the signal V5.

The AND unit 35 performs the AND logic function, but typically it may be accomplished utilizing a nand gate, a commercially available integrated circuit which uses negative logic rather than positive logic, because of its low cost. Of course any circuit which performs the AND logic function is suitable.

FIGS. 2A and 2B illustrate an analog system for the thickness measurement and chatter detection of the invention. In an alternative embodiment, the signal V1 can be digitized and the thickness measurement and chatter detection can be performed digitally. An algorithm for the digital thickness measurement and chatter detection is shown in FIG. 3. The signal V1 is connected to an analog-to-digital convertor 45 to provide a digitized reading for the computations set out in the algorithm.

The thickness T is produced by utilizing a digital lowpass filter 46 and then converting the filter output to a thickness value as shown in the transfer function unit 47. In the embodiment illustrated, $I_n$ is the current digitized detector reading, $F_{n-1}$ is the previous filtered value, $F_n$ is the current filtered value, and a and b are parameters stored in memory. Various other digital filters may be utilized as desired.

In the transfer function computation $A_1$, etc. are parameters stored in memory and 1n indicates the natural logarithm. Other transfer functions may be utilized to compute the thickness, as desired, one such variation being the table look-up transfer function.

The chatter detection portion of FIG. 3 provides for detection of peaks in the signal $I_n$, determination of peak amplitude, determination of peak frequency, and of continued existance of peaks of amplitude and frequency greater than predetermined values. Existance of signals with peaks of sufficient amplitude and of frequency provide for producing a chatter output signal which will light the chatter indicator, and absence of such peaks terminate the chatter output signal and turn off the chatter indicator.

While the word "chatter" is used in the sheet metal rolling field to identify the high frequency variations in thickness resulting from bouncing or chattering of a roll, "chatter" is used herein in a broader sense to identify high frequency cyclical variations in a measured value which is typically but not necessarily, thickness.

We claim:

1. An apparatus for measuring thickness variations in a strip of material moving relative to a gauging station, including in combination:
    a radioactive source positioned at said gauging station for directing radiation to said strip of material;
    a radiation detector positioned at said gauging station for receiving radiation from said source transmitted or reflected by said strip;
    first circuit means having the output of said detector as an input for producing a first electrical signal varying as a function of thickness along said strip, said first signal including a lower frequency component, a higher frequency cyclical component, and a higher frequency noise component;
    a thickness measuring circuit having said first signal as an input and including low pass filter means for substantially removing said higher frequency components of said first signal, and calibration means for providing a second signal as an output varying as a function of said lower frequency component of said first signal;
    a chatter detection circuit having said first signal as an input and including;
    high pass filter means for substantially removing said lower frequency component of said first signal,
    second circuit means having the output of said high pass filter means as an input for providing a third signal varying as a function of frequency of said higher frequency cyclical component,
    a delay unit having said third signal as an input providing a delayed third signal as an output, and
    a chatter indicating unit having said third and delayed third signals as inputs and providing an output indicating presence of chatter in said strip when there is coincidence in time of said third and delayed third signals.

2. An apparatus as defined in claim 1 wherein said second circuit means includes:
    signal amplitude discriminator means having the output of said high pass filter means as an input for providing first output pulses for inputs greater than a predetermined magnitude;
    integrator means having said first pulses as an input for providing a second output pulse varying in amplitude as a function of frequency of said first output pulses over a given time; and
    comparator means having said second pulse as an input for providing a third output pulse as said third signal when said second pulse is greater than a predetermined value.

3. An apparatus as defined in claim 2 including:
    an analog-to-digital converter having the output of said high pass filter means as an input for providing an output varying as a function of the amplitude of said higher frequency components; and
    means connecting said chatter indicating unit output to said converter for gating said converter output on only when chatter is indicated by said unit.

4. An apparatus as defined in claim 3 including:
    a frequency counter having said first output pulses as an input for providing an output varying as a function of the frequency of said first output pulses; and
    means connecting said chatter indicating unit output to said counter for gating said counter output on only when chatter is indicated by said unit.

5. An apparatus as defined in claim 4 including:
means for generating a speed signal varying as a function of the relative speed of said strip and gauging station;
a wavelength calculating unit having said speed signal and second output pulse as inputs for providing an output varying as a function of the wavelength of said higher frequency cyclical component; and
means connecting said chatter indicating unit output to said calculating unit for gating said calculating unit output on only when chatter is indicated by said indicating unit.

6. An apparatus for measuring thickness variations in a strip of material moving relative to a gauging station, including in combination:
a radioactive source positioned at said gauging station for directing radiation to said strip of material;
a radiation detector positioned at said gauging station for receiving radiation from said source transmitted or reflected by said strip;
first circuit means having the output of said detector as an input for producing a first electrical signal varying as a function of thickness along said strip, said first signal including a lower frequency component, a higher frequency cyclical component, and a higher frequency noise component;
an analog to digital converter for converting said first signal to a digital signal;
thickness computing means having said digital signal as an input and including low pass filter means for substantially removing said higher frequency components, and calibration means for providing a second signal as an output varying as a function of said lower frequency component;
chatter computing means having said digital signal as an input and including:
means for detecting peaks in said digital signal greater than a predetermined value,
means for detecting repetition of said peaks at a frequency above a predetermined value, and
means for indicating presence of chatter when peaks are repeating.

7. An apparatus for measuring thickness variations in a strip of material moving relative to a gauging station, including in combination:
a radioactive source positioned at said gauging station for directing radiation to said strip of material;
a radiation detector positioned at said gauging station for receiving radiation from said source transmitted or reflected by said strip;
first circuit means having the output of said detector as an input for producing a first electrical signal varying as a function of thickness along said strip, said first signal including a lower frequency component, a higher frequency cyclical component, and a higher frequency noise component;
thickness measuring means having said first signal as an input and including means for substantially removing said higher frequency components of said first signal, and calibration means for providing a second signal as an output varying as a function of said lower frequency component; and
chatter detection means having said first signal as an input and including means for detecting peaks in said first signal of an amplitude greater than a predetermined value and repeating at a frequency greater than a predetermined value.

8. An apparatus for measuring variations in a stream of material moving relative to a gauging station, including in combination:
a sensor positioned at said gauging station for producing a first electrical signal varying as a function of material at said station, said first signal including a lower frequency component, a higher frequency cyclical component, and a higher frequency noise component;
low frequency measuring means having said first signal as an input and including means for substantially removing said higher frequency components of said first signal, and calibration means for providing a second signal as an output varying as a function of the magnitude of said lower frequency component; and
chatter detecting means having said first signal as an input and including means for detecting peaks in said first signal of an amplitude greater than a predetermined value and repeating at a frequency greater than a predetermined value.

9. A process for measuring thickness variations in a strip of material moving relative to a gauging station, including the steps of:
directing radiation onto said strip of material at said gauging station and detecting such radiation transmitted or reflected by said strip with the detected radiation varying as a function of thickness along said strip;
producing a first electrical signal varying in time as a function of said detected radiation, said first signal including a lower frequency component, a higher frequency cyclical component, and a higher frequency noise component;
in a first circuit removing substantially all of said higher frequency components of said first signal and providing a second signal varying as a function of said lower frequency component of said first signal and corresponding to the thickness of said strip of material;
in a second circuit removing substantially all of said lower frequency component of said first signal and providing a third signal varying as a function of frequency of said higher frequency cyclical component;
delaying said third signal a predetermined period of time providing a delayed third signal; and
combining said third and delayed third signals and providing an output indicating presence of chatter in said strip when there is coincidence in time of said third and delayed third signals.

10. A process as defined in claim 9 including:
generating first output pulses of substantially uniform magnitude and duration for first signal peaks greater than a predetermined magnitude;
integrating said first output pulses to provide a second output pulse varying in amplitude as a function of frequency of said first output pulses over a given time; and
comparing said second pulse with a predetermined reference to provide a third pulse as said third signal when said second pulse is greater than said reference.

11. A process as defined in claim 10 including:
converting said higher frequency components to a digital signal varying as a function of the amplitude of said higher frequency components; and providing said digital signal as another output when chatter is indicated.

12. A process as defined in claim 11 including:
counting the frequency of said first output pulses to determine the frequency of said first output pulses; and
providing said frequency as another output when chatter is indicated.

13. A process as defined in claim 12 including:
measuring the relative speed of said strip and gauging station to provide a speed signal;
combining said speed signal and said second output pulse to determine the wavelength of said higher frequency cyclical component; and
providing said wavelength as another output when chatter is indicated.

14. A process for measuring thickness variations in a strip of material moving relative to a gauging station, including the steps of:
directing radiation onto said strip of material at said gauging station and detecting such radiation transmitted or reflected by said strip with the detected radiation varying as a function of thickness along said strip;
producing a first electrical signal varying in time as a function of said detected radiation, said first signal including a lower frequency component, a higher frequency cyclical component, and a higher frequency noise component;
removing substantially all of said higher frequency components of said first signal and providing a second signal varying as a function of said lower frequency component of said first signal and corresponding to the thickness of said strip of material; and
detecting peaks in said first signal of an amplitude greater than a first predetermined value and repeating at a frequency greater than a second predetermined value and providing a third signal indicating presence of said higher frequency cyclical component of amplitude and frequency exceeding said values as an output indicating presence of chatter in said strip.

15. A process as defined in claim 14 including producing said first electrical signal in analog form.

16. A process as defined in claim 14 including producing said first electrical signal in digital form.

17. A process for measuring variations in a stream of material moving relative to a gauging station, including the steps of:
producing a first electrical signal varying as a function of material at said station and varying in time as a function of said detected radiation, said first signal including a lower frequency component, a higher frequency cyclical component, and a higher frequency noise component;
removing substantially all of said higher frequency components of said first signal and providing a second signal varying as a function of said lower frequency component of said first signal; and
detecting peaks in said first signal of an amplitude greater than a first predetermined value and repeating at a frequency greater than a second predetermined value and providing a third signal as an output indicating presence of said higher frequency cyclical component of amplitude and frequency exceeding said values.

* * * * *